United States Patent
Kleiman et al.

(10) Patent No.: US 7,304,177 B2
(45) Date of Patent: Dec. 4, 2007

(54) METHOD FOR IMPROVING SPREADING PROPERTIES OF COSMETIC INGREDIENTS

(75) Inventors: Robert Kleiman, Mesa, AZ (US); Sambasivarao Koritala, Tempe, AZ (US); John C. Hill, Mesa, AZ (US)

(73) Assignee: International Flora Technologies, Ltd., Chandler, AZ (US)

( * ) Notice: Subject to any disclaimer, the term of this patent is extended or adjusted under 35 U.S.C. 154(b) by 104 days.

(21) Appl. No.: 10/683,787

(22) Filed: Oct. 10, 2003

(65) Prior Publication Data

US 2005/0079191 A1    Apr. 14, 2005

(51) Int. Cl.
*C07C 69/02* (2006.01)
*C07C 69/12* (2006.01)
*C07C 69/34* (2006.01)

(52) U.S. Cl. .................. 560/265; 560/263; 560/261

(58) Field of Classification Search .............. 560/239, 560/241.1, 242
See application file for complete search history.

(56) References Cited

U.S. PATENT DOCUMENTS 6,706,768 B2 * 3/2004 Brown et al. ................ 516/74

FOREIGN PATENT DOCUMENTS

SU        1432054    * 10/1998

OTHER PUBLICATIONS

Sarabia et al. A macrolactonization approach to the stevastelins, Tetrahedron Letters, Apr. 15, 2002, pp. 2961-2965.*
Burke et al., Formal Synthesis of Uvaricin via Palladium-Mediated Double Cyclization, Org. Lett., 3 (12).*
Brown et al. Journal of Organic Chemistry (1988), 53(2), 246-50, Chemical Abstracts online citation.*
Serebryakov et al., Izvestiya Akademii Nauk SSSR, Seriya Khimicheskaya (1987), (1), 114-18, Chemical Abstracts online citation.*
Kleinman, Chemistry of New Oilseed Crops, Janick and Simons (eds.) 1990.*
Wisniak, The Chemistry and Technology of Jojoba Oil, 1987, p. 1.*

* cited by examiner

*Primary Examiner*—Karl Puttlitz
(74) *Attorney, Agent, or Firm*—Norblitt & Gilmore, LLC

(57) ABSTRACT

Described is a method for improving the spreading properties of fatty alcohol containing cosmetic ingredients by providing a fatty alcohol containing starting material and adding an effective amount of acylating source [e.g., $R_1C(=O)OC(=O)R_2$, where $R_1$ is an alkyl substituent of the acyl group having between 1 and 5 carbons; where $R_2$ is a long chain fatty alkyl subsistent (non-limiting examples are unsaturated substituents such as $CH_3—(CH_2)_7—CH=CH—CH_2—(CH_2)_x—$, and saturated substituents such as $CH_3—(CH_2)_y—$, wherein x ranges from 4 to 12, and y ranges from 14 to 22, and the like)], wherein the spreading properties of the starting material are increased over the spreading properties originally exhibited.

4 Claims, 1 Drawing Sheet

Spread Percentages of Fatty Oils/Acetates and Fatty Alcohols/Acetates

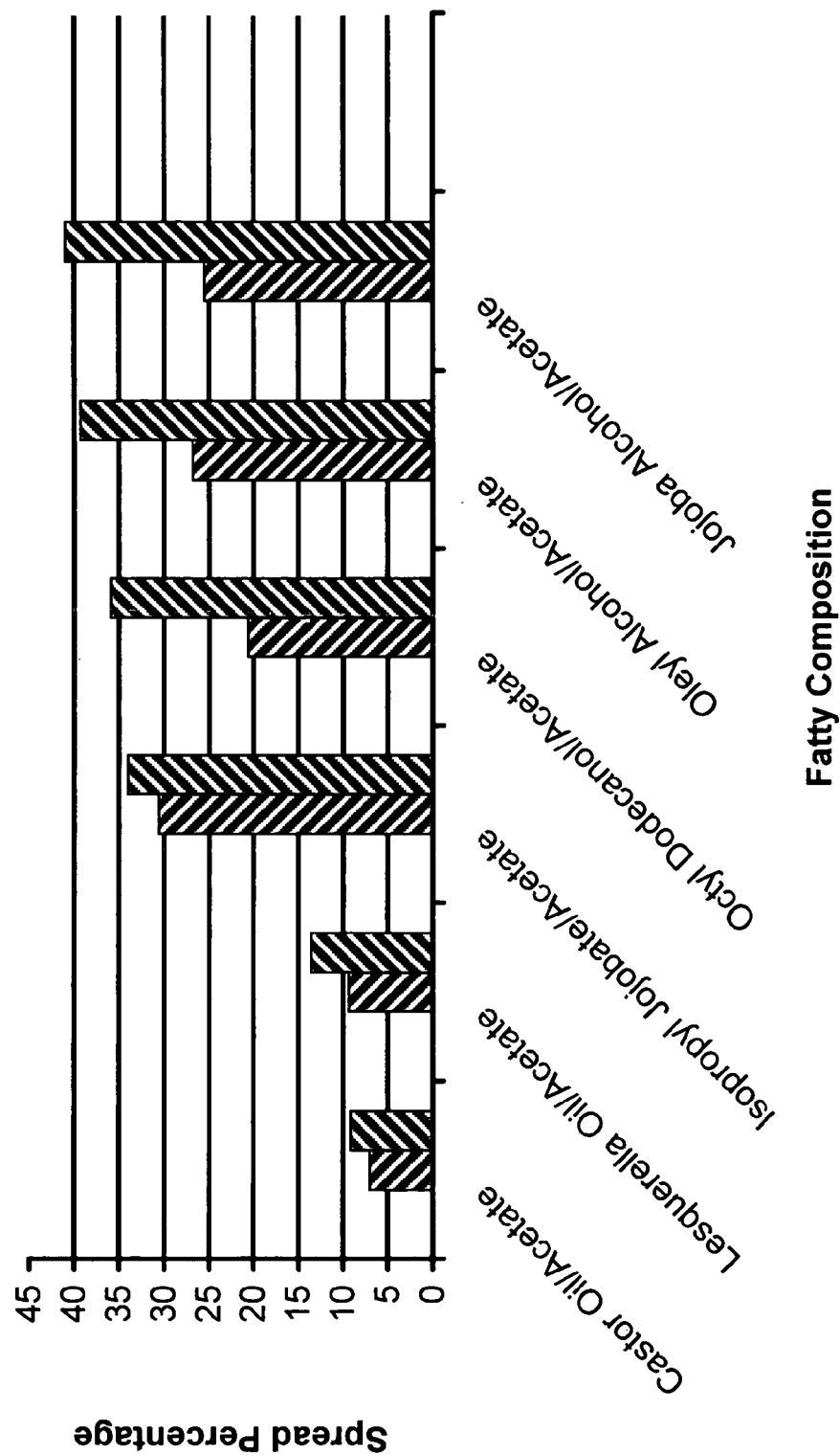

METHOD FOR IMPROVING SPREADING PROPERTIES OF COSMETIC INGREDIENTS

FIELD OF THE INVENTION

The present invention relates to methods for dramatically improving the spreading properties of cosmetic ingredients and uses of the same. More specifically, representative embodiments of the present invention relate to improved spreading properties exhibited by fatty alcohols after they have been acylated.

BACKGROUND

Emollients are materials that are applied to the skin of subjects to produce softness or smoothness. They have been used for centuries in both cosmetic and pharmaceutical products. Historically, natural emollients were obtained from extracts or directly concentrated materials from plants or animals, while modern emollients also include partially synthetic (e.g., derivatives of natural products) or completely synthetic materials.

One of the properties that emollients exhibit is that of spreadability. Generally, the pharmaceutical, cosmetic and personal care industries have viewed spreadability as a dual property where some products benefit by using emollients with high spreadability (e.g., lotions) and other products benefit by using emollients with low spreadability (e.g., lipsticks).

Therefore, there is a current and continuing need for emollient type compositions with improved spreading properties.

SUMMARY OF INVENTION

A representative application of the present invention provides a method for improving the spreading properties of fatty alcohol containing compositions comprising the step of acylating an effective amount fatty alcohols in the fatty alcohol containing composition, whereby the spreading properties are increased over the spreading properties originally exhibited.

A representative application of the present invention provides a method, as described above, wherein acylation comprises the steps of providing an amount of fatty alcohol containing composition, and adding an effective amount of acylating source to the fatty alcohol containing composition.

A representative application of the present invention provides a method, as described above, wherein the acylating source comprises acetyl chloride, acetic anhydride, butyryl chloride, butyric anhydride, propyryl chloride or propyric anhydride.

A representative application of the present invention provides a method, as described above, wherein the fatty alcohol containing composition comprises an oil or wax that contains fatty alcohols.

A representative application of the present invention provides a method, as described above, wherein the fatty alcohol containing composition comprises a relatively pure fatty alcohol.

A representative application of the present invention provides a method, as described above, wherein the fatty alcohols have one free hydroxy group, which may be a primary, secondary or tertiary alcohol.

It is a still further object of the present invention to provide a method, as described above, wherein the fatty alcohols have more than one free hydroxyl group, which may correspond to a primary, secondary or tertiary alcohols.

A representative application of the present invention provides a method, as described above, wherein the fatty alcohols are saturated.

A representative application of the present invention provides a method, as described above, wherein the fatty alcohols are at least mono-unsaturated.

A representative application of the present invention provides a method for improving the spreading properties of fatty alcohol containing compositions comprising the steps providing an amount of fatty alcohol containing composition, and adding an effective amount of acylating source to the fatty alcohol containing composition, where the acylating source is $R_1C(=)OC(=O)R_2$, where $R_1$ is an alkyl substituent of the acyl group having between 1 and 5 carbons; where $R_2$ is an organic residue, and wherein the spreading properties of the starting material are increased over the spreading properties originally exhibited.

DETAILED DESCRIPTION OF REPRESENTATIVE EMBODIMENTS

The present invention is a method, products and uses for the same that find use in the pharmaceutical, personal care and cosmetic industries. Fatty compositions containing fatty alcohols (and fatty alcohols by themselves) are common ingredients in cosmetic and personal care products. These compositions are typically used as emollients, carriers and spreading agents in pharmaceuticals, cosmetics or personal care products.

It has been surprisingly discovered that the process of acylation will increase the spreading properties of fatty alcohols and fatty alcohol containing compositions (e.g., compositions containing at least one free hydroxyl group). A representative embodiment of a fatty alcohol acylation reaction can be illustrated as;

Acyl Source+Fatty Alcohol→Acylated Fatty Alcohol+ residue.

This reaction typically follows one of the below two representative specific reactions:

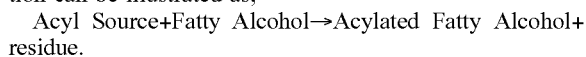

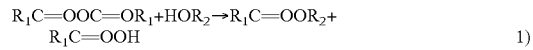

or

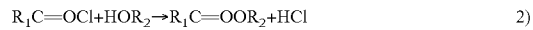

where $R_1$ is an alkyl substituent of the acyl group having between 1 and 5 carbons; where $R_2$ is a long chain fatty alkyl subsistent (non-limiting examples are unsaturated substituents such as $CH_3—(CH_2)_7—CH=CH—CH_2—(CH_2)_x—$, and saturated substituents such as $CH_3—(CH_2)_y—$, wherein x ranges from 4 to 12, and y ranges from 14 to 22, and the like); other fatty alcohols may be used and still fall within the scope of the present invention). Further, these fatty alcohols monohydric or greater; primary, secondary or tertiary alcohols; and/or saturated, mono or greater unsaturated. Finally, other reactions that have the effect of producing an acylated fatty alcohol, such as certain transesterification reactions, may be used and still fall within the scope of the present invention.

FIG. 1 shows the increase in spreading value of fatty oils, which contain fatty alcohols, and fatty alcohols along with the acetates of these fatty oils and alcohols. Representative fatty oil examples include: castor oil, having a spread value of 7.0%; castor oil acetate, having a spread value of 9.1% (this is an increase of 30% relative to castor oil); lesquerella oil, having a spread value of 9.3%; lesquerella oil acetate, having a spread value of 13.6% (this is an increase of over 46% relative to lesquerella oil); isopropyl jojobate, having a spread value of 30.6%; isopropyl jojobate acetate, having a spread value of 34.0% (this is an increase of over 11% relative to isopropyl jojobate). Representative fatty alcohols include: octyl dodecanol, having a spread value of 20.6; octyl dodecanol acetate, having a spread value of 35.9% (this is an increase of over 74% relative to octyl dodecanol); oleyl alcohol, having a spread value of 26.8%; oleyl alcohol acetate, having a spread value of 39.3% (this is an increase of nearly 47% relative to oleyl alcohol); jojoba alcohol, having a spread value of 25.5%; jojoba alcohol acetate, having a spread value of 41.0% (this is an increase of over 60% relative to jojoba alcohol).

Thus it is readily seen that the acylation of fatty alcohol containing compositions yields dramatic improvements in the spreadability of the compositions.

Spreadability testing was performed using a FLORATECH (Chandler, Arizona, USA) method of adding 20 drops the material to be tested on P5 filter paper obtained from Fisher Scientific (Waltham, Massachusetts, USA). The percentage of the whole paper that was covered by the composition in question is measured after 10 minutes and recorded as the percent spread increase value. Samples were tested five times and the results averaged.

A representative formulation may include:

Sunscreen with enhanced spreading properties.

| Phase | INCI Name | % wt./wt. |
|---|---|---|
| A. | Water | 41.65 |
|  | Sodium Dicocoylethylenediamine PEG-15 Sulfate (and) Sodium Lauroyl Lactylate | 1.00 |
|  | Glycerin | 6.00 |
|  | Xanthan Gum | 0.30 |
|  | Disodium EDTA | 0.20 |
| B. | Behenyl Alcohol (and) Glyceryl Stearate (and) Glyceryl Stearate Citrate (and) Sodium Dicocoylethylenediamine PEG-15 Sulfate | 5.25 |
|  | Jojoba Alcohol Acetate | 5.40 |
|  | Jojoba Esters | 6.40 |
|  | Tridecyl Salicylate | 5.00 |
|  | Ethylhexyl Methoxycinnamate | 6.00 |
|  | Butyl Methoxydibenzoylmethane | 1.00 |
|  | Tocopheryl Acetate | 1.00 |
|  | VP/Eicosene Copolymer | 1.00 |
| C. | Isononyl Isononanoate (and) Titanium Dioxide (and) Alumina (and) Simethicone (and) Polyglyceryl-6 Ricinoleate | 7.0 |
| D. | Carbomer | 10.00 |
| E. | Hydrolyzed Jojoba Esters (and) Water (aqua) | 1.00 |
|  | Water | 0.80 |
|  | Phenoxyethanol (and) Methylparaben (and) Ethylparaben (and) Butylparaben (and) Propylparaben (and) Isobutylparaben | 1.00 |
|  | Total | 100.00 |

Mixing Procedure:
1. Add disodium EDTA to the water of Phase A with stirring at 75° C. Add sodium dicocoylethylenediamine PEG-15 sulfate and sodium lauroyl lactylate and glycerin with stirring until completely mixed.
2. Combine all ingredients of Phase B and mix completely at 75° C. Add Phase B to Phase A with rapid stirring.
3. With homomixer agitation, add Phase C to Phase AB at 75° C.
4. Add the Carbomer solution into Phase ABC with rapid stirring at 75° C.
5. Reduce the mix temperature to 55° C. Add Phase E ingredients with stirring.
6. Cool to room temperature.

The compositions of the present invention are found to be most useful in pharmaceutical, cosmetic and personal care applications including, but not limited to: burn lotions and creams; cosmetic creams, lotions, and liquid foundations; massage oils and the like; pressed products such as eye shadow, blush, and powder; molded products such as lipstick, lip balm, foundation, blush, eye liner, eye shadow, mascara and the like; hair care products, such as leave-in conditioners, relaxers, hair dyes and other like compositions where high spreadability is a benefit.

Additional Materials

In addition to the representative ingredients in the compositions of the present invention, further materials may be present for functional or aesthetic reasons. Antioxidants, including tocopherols and tocotrienols (compounds homologous to tocopherols that differ by the presence of three unsaturated bonds in the phytyl side chain), and oryzanol (a mixture of ferulic acid esters of sterols, e.g., beta-sitosteryl ferulate and methyl ferulate, and triterpene alcohols, e.g., 24-methylenecycloartenyl ferulate; see Bailey's Industrial Oil and Fat Products, 4$^{th}$ Ed., John Wiley, New York, 1979, volume 1, pages 407 to 409) may be present. Fragrances, colorants (e.g., dyes or pigments), topically applied medications, UV absorbers, whitening agents, emulsifying agents, binders, scrubbing particulates, and the like may be present.

Additional fatty elements may be selected from mineral oils like paraffin or petroleum oils, silicone oils, vegetable oils like coconut, almond, apricot, corn, jojoba, olive, avocado, sesame, palm, eucalyptus, rosemary, lavender, pine, thyme, mint, cardamon, orange blossoms, soy beans, bran, rice, colza, and castor oils, animal oils and fats like tallow, lanolin, butter oil, fatty acid esters, fatty alcohol esters, waxes whose melting point is the order of the skin's (animal waxes like bee's wax, carnuba or candelilla waxes, mineral waxes like micro-crystalline waxes and synthetic waxes like polyethylene or silicone waxes). All acceptable oils used in cosmetology may be used, like the ones that have been mentioned in CTFA's book, Cosmetic Ingredient Handbook, First edition, 1988, The Cosmetic, Toiletry and Fragrance Association, Inc., Washington ("CTFA").

Cosmetically or dermatologically active substances may be added to the composition of the present invention, meaning active cosmetics chosen from anti-acne agents, anti-microbial agents, anti-perspiration agents, astringents, deodorants, hair removers, external analgesics, agents for hair conditioning, skin conditioning, sun protection, vitamins, catechines, flavonoids, ceramides, fatty substances, polyunsaturated fatty acids, essential fatty acids, keratolytic agents, enzymes, anti-enzymes, moisteners, anti-inflammatory substances, detergents, perfumes, and mineral substances for synthetic coverings. These substances may represent from 1 to 20% by weight of the total weight of the composition.

Detergent or foaming agents, for example, may include disodic cocoamphodiacetate salts; lauroylether sulfosuccinate disodic salts; the vegetable protein acylates; the cocoyl glutamate triethanolamine salts; the lauroyl sarcosinate sodium salts; the glucoside decyl-ethers; and the sodium sulfate lauroyl ethers.

Pasty active compounds (compounds with extremely low spreadability) like lanolin by-products (acetyl lanolin, lanolin, and lanolin alcohols; cholesterol by-products, cholesterol esters (12 cholesteryl hydroxy stearate); pentaerythritol hydroxylated esters, linear mono-esters like butyl stearate, arachidyl propionate or stearyl heptanoate, and triglycerides with a fatty chain less that $C_{16}$ can also be used. These substances may be water-soluble, lipid-soluble, or lipid-soluble and water soluble at the same time, or dispersible. They can be chosen from the compounds that are in CTFA at pages 51 to 101.

Surface active agents, cationic, anionic, non-ionic and/or Zwitterionic may be used. These surface agents may be chosen, for example, from: hydrophilic surface agents (like glycols, such as hexylene glycol, butylene-1,2 glycol, ethyl-2-hexyl sulfosuccinate); mono and diglycerides; oxyethylene octylphenol, and the salts derived from cocoyl and lauroyl collagen; sorbitan palmitate, and the polyoxyethylene by-products of sorbitol palmitate esters; and fatty quaternary ammonium salts. Suitable anionic surfactants which may be used include the water-soluble alkali metal or ammonium salts having alkyl radicals containing from about 8 to about 22 carbon atoms, the term alkyl being used to include the alkyl portion of higher acyl radicals. Examples of suitable synthetic anionic surfactants are sodium or ammonium alkyl sulfates, especially those obtained by sulfating higher ($C_8$-$C_{18}$) alcohols produced, for example, from tallow or coconut oil; alkyl ($C_9$-$C_{20}$) benzene sulfonates, particularly sodium linear secondary alkyl ($C_{10}$-$C_{15}$) benzene sulfonates; alkyl glyceryl ether sulfates, especially those ethers of the higher alcohols derived from tallow or coconut oil and synthetic alcohols derived from petroleum; coconut oil fatty monoglyceride sulfates and sulfonates; salts of sulfuric acid esters of higher ($C_8$-$C_{18}$) fatty alcohol-alkylene oxide, particularly ethylene oxide reaction products; the reaction products of fatty acids such as coconut fatty acids esterified with isoethionic acid and neutralized with sodium hydroxide; sodium and potassium salts of fatty acid amides of methyl taurine; alkane monosulfonates such as those derived from reacting alpha-olefins ($C_8$-$C_{20}$) with sodium bisulfite and those derived from reacting paraffins with $SO_2$ and $Cl_2$ and then hydrolyzing with a base to produce a random sulfonate; and olefin sulfonates which term is used to describe the material made by reacting olefins, particularly $C_{10}$-$C_{20}$ alpha-olefins, with $SO_3$ and then neutralizing and hydrolyzing the reaction product. The preferred anionic surfactants are sodium or ammonium ($C_{10}$-$C_{18}$) alkyl sulfates and ($C_{10}$-$C_{18}$) alkyl polyethoxy (1-11 EO, ethylene oxide) sulfates and mixtures thereof having differing water solubilities.

Particularly preferred anionic surfactants comprise a mixture of a $C_{10}$-$C_{18}$ alkyl sodium or ammonium sulfate or sulfonate or a $C_{14}$-$C_{18}$ alpha-olefin sodium or ammonium sulfonate (AOS) and a $C_8$-$C_{12}$ alkyl polyethoxy (2-4 EO) sodium or ammonium sulfate. Mixtures containing a major amount of the alkyl sulfates, olefin sulfonates or alkyl alkoxy sulfates with aryl sulfonates such as sodium cumene sulfonate, sodium xylene sulfonate and sodium benzene sulfonate are also optional.

The amount of anionic surfactant present in the composition will generally range from about 0 or 1% or 4 to 12% total ingredients by weight. The amphoteric or Zwitterionic surfactant, may optionally be present at a level of at least about 0.1 or at least about 0.25 percent by weight of the total composition, per 1 part by weight of the content of anionic surfactant present in the composition.

Examples of amphoteric surfactants that may be used in the composition of the invention are betaines and compounds that can be broadly described as derivatives of aliphatic secondary and tertiary amines in which the aliphatic radical can be straight chain or branched and wherein one of the aliphatic substituent contains from about 8 to 18 carbon atoms and one contains an ionic water solubilizing group, e.g., carboxy, sulfonate, sulfate, phosphate, or phosphonate. Examples of compounds falling within this definition are sodium 3-dodecylaminopropionate, sodium 3-dodecylaminopropane sulfonate, N-alkyltaurines, such as prepared by reacting dodecylamine with sodium isethionate, higher N-alkyl aspartic acids and the products sold under the trade name "MIRANOL (Rhodia Inc., Cranbury, New Jersey, USA).

Makeup or cosmetic compositions in accordance with the present invention may also contain as an optional ingredient, a film forming skin tightening agent, particularly a plant derived biological polysaccharide cosmetic ingredient that may be combined with a casein hydrolysate.

The polysaccharides that can be used in the practice of the invention include, for example, lecithin, pectin, karaya gum, locust bean gum, xanthan gum and mixtures thereof. The polysaccharides are preferably used in the present compositions in combination with a casein hydrolysate.

Suitable co-emulsifiers are both known w/o (water in oil) and o/w (oil in water) emulsifiers. Typical examples of fats are glycerides while suitable waxes include *inter alia* beeswax, paraffin wax or microwaxes. Suitable thickeners include, for example, crosslinked polyacrylic acids and derivatives thereof, polysaccharides, more particularly xanthan gum, guar guar, agar agar, alginates and tyloses, carboxyl-methyl cellulose and hydroxyethyl cellulose, also fatty alcohols, monoglycrides and fatty acids, polyacrylates, polyvinyl alcohol and polyvinyl pyrrolidone. In the context of the invention, biogenic agents include, for example, plant extracts, protein hydrolysates and vitamin complexes. Typical film-formers include polyvinyl pyrolidone, vinyl pyrolidone/vinyl acetate copolymers, polymers of the acrylic acid series, quaternary cellulose derivatives and similar compounds. Suitable preservatives include, for example formaldehyde solution, p-hydroxybenzoate or sorbic acid. Suitable pearl esters include, for example, glycol distearic acid esters, such as ethylene glycol distearate, and also fatty acids and fatty acid monoglycol esters. The dyes used may be selected from many of the substances that are permitted and suitable for cosmetic purposes, as listed for example in the publication "Kosmetische Farbemittel" of the Farbstoffkommission der Deutschen pages 81-106. These dyes are typically used in concentrations of 0.001 to 0.1% by weight, based on the mixture as a whole.

The total percentage content of auxiliaries and additives may be 1 to 50% by weight and may be 5 to 40% by weight, based on the formulation. The formulations may be produced in any known manner, e.g., by hot, cold, hot/cold or PIT emulsification. These are purely mechanical processes that do not involve a chemical reaction. The cosmetic and/or pharmaceutical formulations may have a water content of 25 to 95% by weight and preferably 50 to 75% by weight.

Representative embodiments of the invention are described above in the Drawings and Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s). The foregoing description of representative embodiments and best mode of the invention known to the applicants at the time of filing the application has been presented and is intended for the purposes of illustration and description. It is not intended to be exhaustive or to limit the invention to the precise form disclosed, and many modifications and variations are possible in the light of the above teachings. Representative embodiment have been chosen and described in order to best explain the principles of the invention and their practical application and to enable others skilled in the art to best utilize the invention in various embodiments and with various modifications as are suited to the particular use contemplated.

What is claimed is:

1. A method for improving the spreading properties of a topical cosmetic formulation, said method comprising the steps of:
   providing a fatty alcohol containing starting material, comprising at least one of castor oil, lesquerella oil, isopropyl jojobate, octyl dodecanol, oleyl alcohol and jojoba alcohol;
   acylating said starting material with an acylating agent having between 1 and 5 carbons to produce an acylated product that demonstrates increased spreading properties as compared with the spreading properties of the starting material prior to acylation; and
   compounding the acylated product in at least one of a cream, a lotion, a liquid foundation, massage oil, a pressed cosmetic product, an eye shadow, a blush, a powder, a semi-and solid foundation, a molded cosmetic product, a lipstick, a lip balm, an eyeliner, a mascara, a hair care product, a conditioner, a relaxer, and a hair dye.

2. The method of claim 1, wherein said step of acylating said starting material comprises introducing at least one acylating agent selected from the group consisting of acetyl chloride, acetic anhydride, butyryl chloride, butyric anhydride, propyryl chloride and propyric anhydride to said starting material.

3. The method of claim 1, wherein said starting material comprises at least one of a wax and an oil.

4. A method for improving the spreading properties of a topical cosmetic formulation, said method comprising the steps of:
   providing a fatty alcohol containing starting material comprising at least one of castoroil, lesquerella oil, isopropyl jojobate, octyl dodecanol, oleyl alcohol and jojoba alcohol;
   introducing at least one acylating agent to said composition, wherein said acylating agent comprises at least one of $R_1C(=O)OC(=O)R$ and $R_1C=OCl$, where $R_1$ comprises an alkyl substituent of the acyl group having between 1 and 5 carbons, and R comprises an organic carbon-containing residue;
   wherein the spreading properties of the resulting acylated product are substantially increased over the spreading properties of the starting material prior to acylation; and
   compounding the acylated product in at least one of a cream, a lotion, a liquid foundation, a massage oil, a pressed cosmetic product, an eve shadow, a blush, a powder, a semi-and solid foundation, a molded cosmetic product, a lipstick, a lip balm, an eyeliner, a mascara, a hair care product, a conditioner, a relaxer, and a hair dye.

* * * * *

UNITED STATES PATENT AND TRADEMARK OFFICE
CERTIFICATE OF CORRECTION

PATENT NO. : 7,304,177 B2
APPLICATION NO. : 10/683787
DATED : December 4, 2007
INVENTOR(S) : Robert Kleiman et al.

It is certified that error appears in the above-identified patent and that said Letters Patent is hereby corrected as shown below:

On the Title Pg Item (57) in the Abstract, 5$^{th}$ line, "$R_1C)$" should be changed to "$R_1C$", removing the parenthesis;

On the Title Pg Item (57) in the Abstract, 7$^{th}$ line, change the word "subsistent" to the word "substituent";

On the Title Pg Item (57) in the Abstract, 11$^{th}$ line, remove the "]" between the word "like)" and the "comma";

Column 2, line 11, add the word "of" after the word "steps";

Column 2, line 15, "$R_1C(=)OC(=O)R_2$" should be changed to "$R_1C(=O)OC(=O)R_2$", adding "O" between "=" and ")";

Column 2, line 56, add "are" between "alcohols" and "monohydric";

Column 3, lines 20-21, add "of" between "drops" and "the material"; and

Column 6, line 11, remove the quotation mark before the word MIRANOL.

Signed and Sealed this

Seventh Day of July, 2009

JOHN DOLL
*Acting Director of the United States Patent and Trademark Office*